(12) United States Patent
Andoh (10) Patent No.: US 9,504,290 B2
(45) Date of Patent: Nov. 29, 2016

(54) WALKING SHOE

(75) Inventor: Masamichi Andoh, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 1116 days.

(21) Appl. No.: 13/608,462

(22) Filed: Sep. 10, 2012

(65) Prior Publication Data

US 2013/0000156 A1    Jan. 3, 2013

Related U.S. Application Data

(63) Continuation of application No. PCT/JP2011/055579, filed on Mar. 10, 2011.

(30) Foreign Application Priority Data

Mar. 16, 2010   (JP) ................................. 2010-058756

(51) Int. Cl.
| | |
|---|---|
| A43B 3/00 | (2006.01) |
| A43B 7/14 | (2006.01) |
| A61B 5/11 | (2006.01) |
| A61B 5/00 | (2006.01) |
| A61H 3/00 | (2006.01) |

(52) U.S. Cl.
CPC ........... *A43B 3/0005* (2013.01); *A43B 7/1455* (2013.01); *A61B 5/1117* (2013.01); *A61B 5/6807* (2013.01); *A61H 3/00* (2013.01); *A61H 2201/0173* (2013.01); *A61H 2201/5048* (2013.01); *A61H 2201/5064* (2013.01); *A61H 2201/5071* (2013.01); *A61H 2201/5084* (2013.01)

(58) Field of Classification Search
CPC  A43B 3/0005; A43B 7/1455; A61B 5/6807; A61B 5/1117; A61H 3/00; A61H 2201/0173; A61H 2201/5064; A61H 2201/5071; A61H 2201/5084; A61H 2201/5048
See application file for complete search history.

(56) References Cited

U.S. PATENT DOCUMENTS

| | | | | |
|---|---|---|---|---|
| 5,724,313 A | * | 3/1998 | Burgess et al. ................ | 367/116 |
| 6,301,964 B1 | * | 10/2001 | Fyfe et al. ....................... | 73/510 |
| 6,704,603 B1 | * | 3/2004 | Gesotti ............... | A61N 1/36003 |
| | | | | 607/62 |

(Continued)

FOREIGN PATENT DOCUMENTS

| | | |
|---|---|---|
| JP | 7-39502 | 7/1995 |
| JP | 8-095487 A | 4/1996 |

(Continued)

OTHER PUBLICATIONS

PCT/JP2011/055579 Written Opinion dated Mar. 24, 2011.

(Continued)

*Primary Examiner* — Rene Towa
(74) *Attorney, Agent, or Firm* — Arent Fox LLP (57) ABSTRACT

A walking shoe that senses a fall and urges a user of the shoe to perform movement for fall prevention. When the walker stumbles or almost falls, a microprocessor is activated, based on a sensing signal of a pressure-sensitive sensor that senses a pressure applied to a tread to detect a lifting velocity and/or a lifting amount of the foot based on a detection signal of an acceleration sensor, and when the lifting velocity and/or the lifting amount is lower than a reference value, the microprocessor actuates a stimulator that stimulates a bottom of the foot. At this time, since the user reflexively lifts the foot, the user can avoid stumbling.

5 Claims, 4 Drawing Sheets

(56) References Cited

U.S. PATENT DOCUMENTS

2005/0097970 A1* 5/2005 Nurse .................. 73/862.041
2012/0059432 A1* 3/2012 Emborg ............ A61N 1/36003
                                                            607/49

FOREIGN PATENT DOCUMENTS

| JP | 10-165395 A | 6/1998 |
| JP | 2001-245705 A | 9/2001 |
| JP | 2003-144482 A | 5/2003 |
| JP | 2006-158431 A | 6/2006 |
| JP | 2009-106387 A | 5/2009 |

OTHER PUBLICATIONS

PCT/JP2011/055579 ISR dated Mar. 24, 2011.

* cited by examiner

WALKING SHOE

CROSS REFERENCE TO RELATED APPLICATIONS

The present application is a continuation of International application No. PCT/JP2011/055579, filed Mar. 10, 2011, which claims priority to Japanese Patent Application No. 2010-058756, filed Mar. 16, 2010, the entire contents of each of which are incorporated herein by reference.

FIELD OF THE INVENTION

The present invention relates to a walking shoe, and particularly to a shoe having a fall prevention function.

BACKGROUND OF THE INVENTION

A situation may occur where not only elderly people but also a generation that is generally unrecognized as the elderly people, for example, people in their late 40 s to 50 s unexpectedly stumble over a step, which they would not have stumbled in their early days. It is considered that this occurs because raising of a foot or an angle of a toe is insufficient, as compared with a walking state under a condition where the people do not stumble. Normally, the people are unaware of this insufficiency, and the foregoing often occurs unconsciously due to age-related weakening eyesight, deterioration of cognitive ability, muscular weakness, and the like. Moreover, an endurance capacity is also deteriorated, and thus, when the people become tired with prolonged walking, a similar phenomenon may be caused.

In Patent Document 1, there is disclosed a walking observing apparatus that detects whether or not abnormal walking occurs in an elderly person wearing the observing apparatus at his or her waist to collect data during walking of the wearer. By giving appropriate prescription to the elderly person in accordance with the collected data, measures to prevent falls or the like are taken.

In Patent Document 2, there is disclosed a fall prevention training assist apparatus including an inclination sensor mounted on a side surface of a supporter to be worn on a foot, a sound generating unit that generates sound by a signal of the inclination sensor, and a pressure sensor mounted on a lower side of a heel of the supporter. An inclination angle of a toe of the foot is sensed by the inclination sensor, and when determined that the inclination angle is insufficient as compared with that of normal walking, the wearer is notified by the sound generated by the sound generating unit to assist, for example, training to normalize walking of an elderly person.

However, the observing apparatus described in Patent Document 1 is intended to observe the walking of the elderly person to collect the data, and is not intended to prevent falls during actual walking.

Patent Document 2 describes that a person stumbles over a doorsill or the like and falls because the inclination angle of the foot is small. However, for example, when the person ascends the step or the like, not only the inclination angle of the foot but also a lifting amount of the foot or a lifting velocity give influence. Therefore, when only the inclination angle of the foot is detected, the person cannot necessarily ascend the step without stumbling. In Patent Document 2, the walker, while listening to the sound generated when the inclination angle of the foot taking a step is at a predetermined level or higher, learns how to walk so as to emit the sound. However, when the person actually almost falls, the apparatus does not sense the fall to urge the person to perform movement for fall prevention.

Patent Document 1: Japanese Unexamined Patent Publication No. H10-165395
Patent Document 2: Japanese Unexamined Patent Publication No. 2006-158431

SUMMARY OF THE INVENTION

An object of the present invention is to provide a walking shoe that senses a fall when a walker stumbles or almost falls, and urges the walker to perform movement for fall prevention.

In order to achieve the above-described object, a first embodiment of the present invention provides a walking shoe including: a shoe body that receives a foot, a stimulator that is mounted on the shoe body and stimulates a bottom of the foot, an acceleration sensor that is mounted on the shoe body, and capable of detecting an acceleration in a direction parallel to ground acting on the shoe body and an acceleration in a direction perpendicular to the ground, and a microprocessor that is mounted on the shoe body, detects a lifting velocity and/or a lifting amount of the foot, based on a detection signal of the acceleration sensor, and actuates the stimulator when determined that the lifting velocity and/or the lifting amount is lower than a reference value.

A second embodiment of the present invention provides a walking shoe including: a shoe body that receives a foot, a stimulator that is mounted on the shoe body and stimulates a bottom of the foot, an acceleration sensor that is mounted on the shoe body, and capable of detecting an acceleration in a direction parallel to ground acting on the shoe body and an acceleration in a direction perpendicular to the ground, a ranging sensor that is mounted on a front end portion of the shoe body, and detects a distance between the shoe body and a front obstacle, and a microprocessor that is mounted on the shoe body, determines whether or not there is a possibility that the shoe body collides with the front obstacle from a detection signal of the acceleration sensor and a detection signal of the ranging sensor, and actuates the stimulator when determined that the shoe body collides.

During walking, as long as a foot taking a step has a sufficient height, a user does not stumble. This height is roughly decided by the lifting amount of the foot (or thigh) and an angle of a toe. There are differences among individuals in the manner of walking, and a raising amount of the thigh and a raising amount of the toe vary among people. In the first embodiment, when the walking starts, the lifting velocity or the lifting amount of the foot is detected based on the detection signal of the acceleration sensor. The lifting velocity can be obtained directly from the signal of the acceleration sensor, and the lifting amount can be obtained by integrating the lifting velocity. When determined that the detected lifting velocity or lifting amount is lower than the reference value, the stimulator is actuated. As described above, with aging and fatigue of the person, the lifting velocity or the lifting amount of the foot incidentally becomes insufficient, resulting in the stumbling. At this time, when any stimulation is received from the bottom of the foot, a human reflexively performs movement of lifting the foot. The present invention utilizes this movement to prevent the stumbling from occurring. While a fixed value set in advance may be used as the reference value, for example, the reference value may also be decided from accumulated data of the past lifting velocity or the lifting amount.

In the second embodiment, whether or not there is a possibility that the shoe body collides with the front obstacle is determined from the detection signal of the acceleration sensor and the detection signal of the ranging sensor, and when determined that the shoe collides with the obstacle, the stimulator is actuated. For example, when ascending a step or stairs, a person decides the lifting amount of the foot while checking the step or the stairs from the past experience, based on information obtained from eyesight, and lifts the foot unconsciously. However, when determined that the lifting amount is insufficient and that a forefront of the shoe will collide with the obstacle, the bottom of the foot is slightly stimulated by the stimulator embedded in the shoe, which can urge the user of the shoe to perform movement for fall prevention.

In the walking shoe of the second embodiment, as a method of the collision determination, for example, a trajectory of the shoe may be calculated based on the detection signal of the acceleration sensor, and whether or not there is a possibility that the shoe body collides with the front obstacle may be determined from the trajectory and the distance between the shoe body and the front obstacle, which has been obtained from the detection signal of the ranging sensor. In this case, accuracy of the collision determination is improved, which can prevent the stimulator from being needlessly actuated.

In the walking shoe of the second embodiment, the microprocessor may determine whether a walking mode is a step ascent mode or a normal walking mode based on the detection signal of the acceleration sensor, and when determined that the walking mode is the step ascent mode, whether or not there is a possibility that the shoe body collides with the front obstacle may be determined. During the normal walking, the lifting velocity or the lifting amount of the shoe is more likely to cause stumbling than the collision of the shoe with an obstacle, whereas when the user ascends a step, the collision with the front obstacle (step or the like) mainly causes stumbling.

A pressure-sensitive sensor to sense a pressure applied to a tread may be mounted on a bottom portion of the shoe body. Since the pressure-sensitive sensor can reliably detect whether or not the foot has landed, the walking state (whether or not the user is walking or the like) can be determined by a sensing signal of the pressure-sensitive sensor. When a piezoelectric element is used as the pressure-sensitive sensor, the pressure-sensitive sensor need not be constantly powered, and applying a pressure from outside allows the signal to be outputted, which enables the pressure-sensitive sensor to be used as a trigger. For example, when a state where the acceleration sensor does not generate the signal lasts for a predetermined time, the microprocessor may be put into a standby state, and by sensing the signal of the pressure-sensing sensor, the microprocessor may be returned to an activated state. That is, when the shoe is not used, the circuit is put into the standby state where power consumption is suppressed, and when the shoe is used, a voltage generated by the pressure-sensitive sensor is sensed to return the circuit from the standby state to the activated state, by which wasteful power consumption can be eliminated.

The microprocessor may have a memory that automatically samples a walking situation for a predetermined period to store a trajectory generated most frequently as a shoe trajectory of a user. In this case, since this shoe itself learns a habit and a situation of the user as a use period elapses, stimulation control in accordance with the user can be performed.

As described above, according to the present invention, when the user almost falls, it is sensed and the bottom of the foot is stimulated, by which the user of the shoe reflectively lifts the foot, thereby preventing stumbling or falls.

DETAILED DESCRIPTION OF THE INVENTION

First Embodiment

Figure 1:
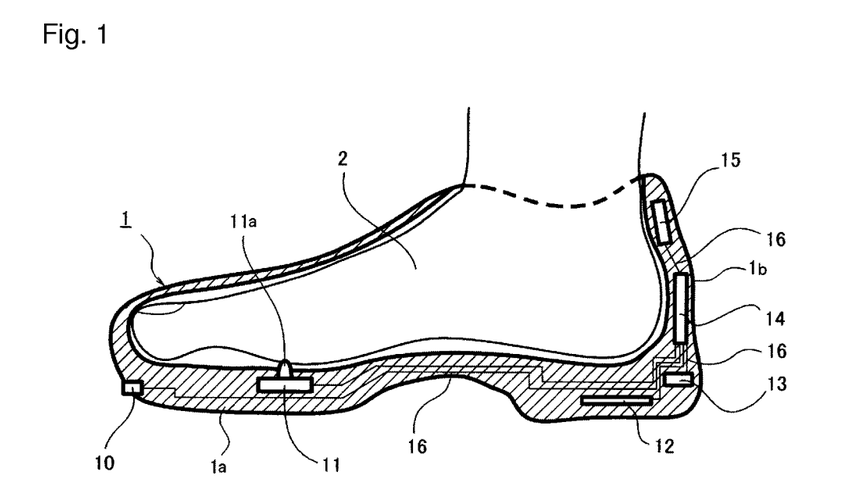
FIG. 1 is a diagram showing a cross section of one example of a shoe of the present invention.

FIG. 1 shows a shoe 1 and a foot 2 of a user. A ranging sensor 10 for sensing an obstacle is mounted on a front end portion of the shoe 1, and a stimulator 11 that stimulates a bottom of the foot is embedded in a sole portion. A pressure-sensitive sensor 12 that senses a pressure applied to a tread is mounted in a tread portion 1a of the shoe 1, for example, in a heel portion and at a position corresponding to a heel. Furthermore, a waist portion 1b (on a rear surface side) of the shoe 1 is provided with an acceleration sensor 13, a microprocessor 14, and a battery 15. Mounting positions of the acceleration sensor 13, the microprocessor 14, and the battery 15 are not limited to those in FIG. 1, and may be embedded in other sites of the shoe 1 such as the tread portion 1a, a lining portion, and the like. These elements are mutually connected through wiring 16.

The ranging sensor 10 is mounted on the front end portion of the shoe 1 to detect a distance to a front step or a front obstacle. As the ranging sensor 10, a publicly known sensor such as an ultrasonic sensor and an infrared sensor can be used.

The stimulator 11 is a device that drives an actuation pin 11a by an actuator in an electromagnetic method, a piezoelectric method, or the like to stimulate the bottom of the foot. Immediately after the bottom of the foot is stimulated, the actuation pin 11a is released from an actuated state so that the bottom of the foot is not excessively stimulated. Accordingly, even if the user enters a state of stepping on the stimulator 11, the pin 11a does not stick in the bottom of the foot. FIG. 1 shows an example of the stimulator 11 in which the actuation pin 11a stimulates the bottom of the foot, however, the present invention is not limited thereto, and a device that gives slight vibration to the bottom of the foot, such as a piezoelectric element and a vibration motor, may be employed.

The pressure-sensitive sensor 12 is a sensor that senses the pressure applied to the tread portion 1a, so as to detect whether or not the shoe 1 has departed from ground. In FIG. 1, the pressure-sensitive sensor 12 is mounted on the heel portion, but the present invention is not limited thereto. The pressure-sensitive sensor 12 is made of, for example, a piezoelectric element or the like, and performs sensing by changing the pressure by walking into electricity. The electricity is continuously generated during walking, and thus, when the electricity is not used for the sensing, this electric power is regenerated in the battery 15, so that drain of the battery 15 can also be prevented. When the power consumption itself is very small, the electric power generated by the pressure-sensitive sensor 12 can be charged. As a material of the piezoelectric element, lead zirconate titanate (PZT), polyvinylidene fluoride (PVDF), polylactic acid (PLLA), or the like can be used. Besides the piezoelectric element, an electret or electrostatic method can also be used.

The acceleration sensor 13 is a biaxial acceleration sensor that senses an acceleration in a direction parallel to the ground (front-back direction), and an acceleration in a direction perpendicular to the ground (up-down direction). In addition to the foregoing, a triaxial acceleration sensor capable of sensing an acceleration in a right-left direction may also be used. A mounting position of the acceleration sensor 13 is not limited to the heel portion as shown in FIG. 1, but any position may be employed.

The microprocessor 14 receives a signal from the acceleration sensor 13 at predetermined time intervals and subjects this signal to arithmetic operation processing, by which a trajectory of the shoe 1 (a lifting velocity, a lifting amount, a forward velocity, a forward amount, an inclination angle, and the like) can be obtained. Also, signals are received from the ranging sensor 10 and a pressure-sensitive sensor 12, so that the distance to a front obstacle can be obtained based on the signal from the ranging sensor 10, and whether or not the shoe 1 has departed from the ground can be determined based on the signal from the pressure-sensitive sensor 12. The microprocessor 14 controls the stimulator 11 based on the signals from the sensors 10, 12, 13. While the microprocessor 14 includes therein an internal memory, the microprocessor 14 may be provided with an external memory.

As the battery 15, a small battery such as a button battery is desirable, and the battery 15 is exchangeable as needed. A solar battery can also be used as the battery 15, and in the case where the pressure-sensitive sensor 12 has an electric generation function, the battery may have a function of storing the generated electric power. Furthermore, a power generating device that generates electric power based on the movement of the shoe may be provided separately.

Figure 2:
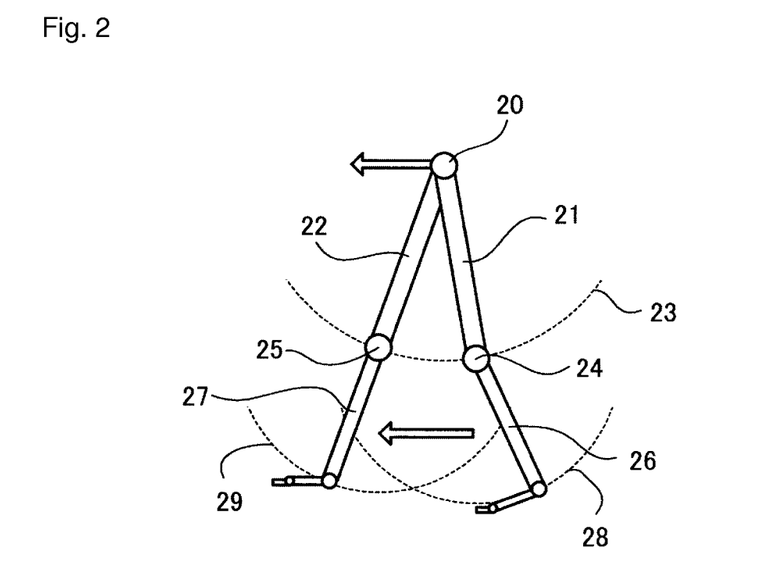
FIG. 2 is a diagram schematically showing movement of a skeletal structure when a person walks.

FIG. 2 schematically shows a skeletal structure when a person is walking. Reference numeral 20 denotes a hip joint, 21, 22 each denote a thigh bone, 24, 25 each denote a knee joint, and 26, 27 each denote a tibial bone, which are modelized. A trajectory 23 indicates a trajectory drawn by the knee joints 24, 25, centering on the hip joint 20. Moreover, a trajectory 28 indicates a trajectory drawn by a forefront of the tibial bone 26, centering on the knee joint 24. Moreover, a trajectory 29 indicates a trajectory drawn by a forefront of the tibial bone 27, centering on the knee joint 25.

During walking, the thigh bones move like pendulums at angles of 20° to 30° centering on the hip joints, and the tibial bones move like pendulums at angles of 40° to 50° centering on the knee joints. The angles are not limited to the foregoing, but vary among individuals, and in each of individual persons, these angles during walking are almost constant. A pelvis moves almost horizontally with respect to a walking direction, the tibial bones move like the pendulums, centering on the knee joints, which are forefronts of the thigh bones moving like the pendulums. Therefore, if an angle of a toe is not considered, the shoe itself moves like a duplex pendulum controlled by muscles. This movement is shown in FIG. 2.

Figure 3:
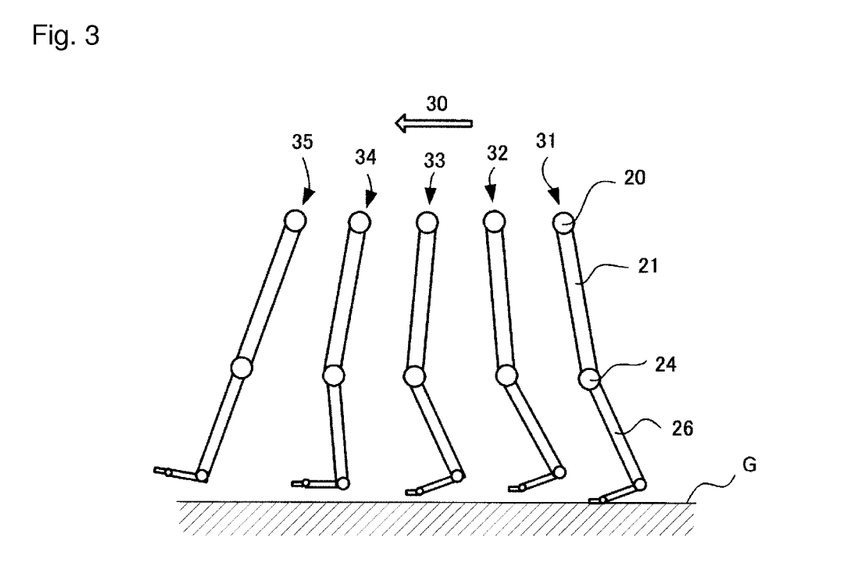
FIG. 3 is a diagram schematically showing movement of a leg during normal walking.

Attention is paid to the movement of one leg during ordinary walking, which is shown in FIG. 3. FIG. 3 focuses on a left leg in FIG. 2, and schematically shows an image as if the left leg during walking is photographed by stroboscope.

Arrow 30 indicates the walking direction. With the movement by walking, a state of the leg changes in order of a state 31, a state 32, a state 33, a state 34, and a state 35. The state 31 indicates a state immediately before the toe kicks up from ground G. Although the hip joint 20 is illustrated to move in parallel to the ground G in the states 31 to 35, actually, slight vertical movement is caused by movement of the other leg.

When shifting from the state 31 to the state 32, the bottom of the foot departs from the ground G in order to carry the foot forward. In the knee joint, the angle is increased in order to lift the toe from the ground G. In the state 33, the thigh bone 21 is swung forward with respect to a body, and at about this point, the knee joint 24 shifts in a direction where it is completely extended (the angle of 0°), and goes through the state 34 to reach the state 35.

This movement when the person walks is almost constantly repeated. The microprocessor 14 monitors the trajectory of the shoe 1 at this time based on the detection signal of the acceleration sensor 13. Since the movement of the shoe 1 has an acceleration in any direction with respect to the ground G at any time point, the movement can be monitored by the acceleration sensor 13.

The microprocessor 14 senses the signal of the acceleration sensor 13 every predetermined period and subjects this sensing signal to the arithmetic operation processing, by which the trajectory of the shoe 1 during normal walking can be obtained. The trajectory of the shoe 1 during normal walking is held in the memory inside the microprocessor 14 after a sampling period. A mechanism may be employed in which the sampling period can be uniquely set by the user of the shoes, or after the user buys the shoes, walking situations for several hours or for several days after the microprocessor 14 is first activated are automatically sampled. The microprocessor 14 stores the trajectory occurring most frequently in the memory as a trajectory of the shoe of the user. As to the determination of the trajectory, a plurality of trajectories are recognized as the same trajectory, using a threshold.

When the shoe 1 is not worn, the microprocessor 14 keeps current consumption to a minimum to suppress consumption of the battery 15. If the acceleration sensor 13 does not react for a predetermined period, the microprocessor 14 enters a standby state, and when receiving the signal from the pressure-sensitive sensor 12, the microprocessor 14 enters an activated state.

If the microprocessor 14 is in the activated state, and the user has started walking, the trajectory of the shoe 1 is determined based on the signal of the acceleration sensor 13. While this trajectory is determined to be within a range of the normal walking, the processing here is only repeated.

Figure 4:
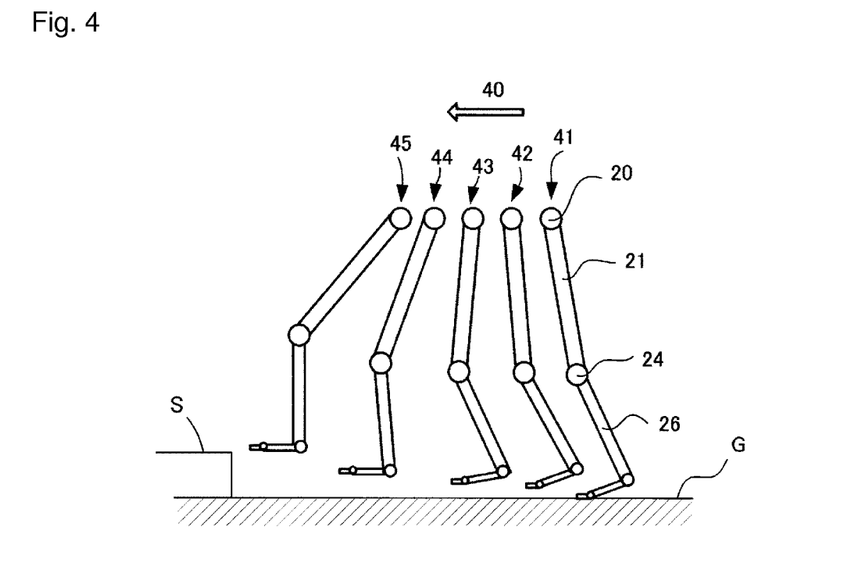
FIG. 4 is a diagram schematically showing movement of the leg when a person ascends a step.

Next, a motion of the leg when the user tries to ascend a step (or an obstacle) S will be described with reference to FIG. 4. When the user ascends stairs, or when the user steps over something, the movement of the leg changes as compared with the movement during the normal walking. Arrow 40 indicates the walking direction, and the state of the leg sequentially changes from a state 41 to a state 45. The forward velocity is reduced from the state 41 to the state 42, and from the state 42 to the state 45, the thigh bone 21 is lifted at a larger angle as compared with the case in FIG. 3. The tibial bone 26 is not swung forward, and forms an angle close to 90° with respect to the ground G. The motion is such that the thigh bone 21 is lifted in synchronization with a velocity at which the user tries to go forward, but when this velocity at which thigh bone 21 is lifted is slow, the user stumbles over the step. The stumbling is likely to occur when the state shifts from the state 43 to the state 44.

In the state 43, the shoe has already departed from the ground G, as compared with the state during the normal walking. Thus, the microprocessor 14 receiving the signal from the acceleration sensor 13 determines that the trajectory of the shoe has changed, and instantly determines that the user has started a motion of overriding the step S to start scanning by the ranging sensor 10.

The trajectory of the foot changes smoothly when it has not landed, and if the acceleration in the direction parallel to the ground and the acceleration in the direction perpendicular to the ground can be sensed, the trajectory of the shoe several milliseconds to several ten milliseconds after this time point can be predicted.

When the ranging sensor 10 senses the step (or an obstacle) S within several ten cm (for example, about 20 cm), the microprocessor 14 instantly calculates a collision time with the step S, based on the predicted trajectory. When a distance between the step S and the shoe is reduced as predicted after a predetermined time has passed, the microprocessor 14 determines that the user will stumble, and activates the stimulator 11 to stimulate the bottom of the foot of the user. The user reflexively lifts the foot by the stimulation given to the bottom of the foot, thereby avoiding the stumbling.

Figure 5:
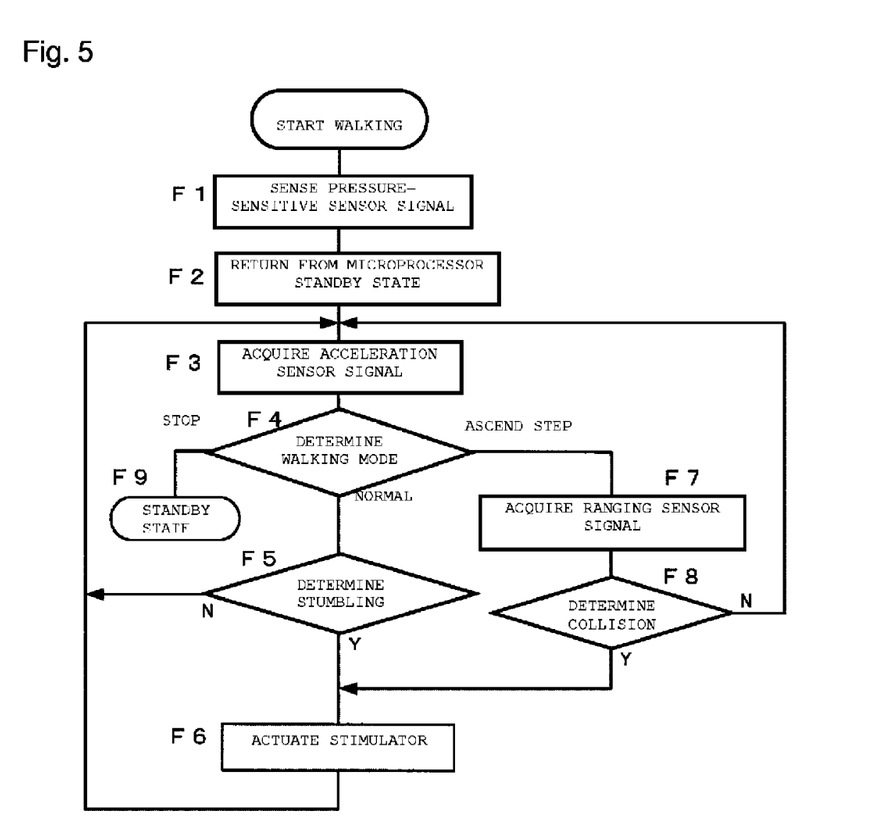
FIG. 5 is a flowchart showing one example of processing algorithm of a microprocessor.

FIG. 5 shows an example of processing algorithm of the microprocessor 14. Before the walking is started, the microprocessor 14 enters the standby state to prevent consumption of the battery. When the signal is inputted from the pressure-sensitive sensor 12 (F1), the microprocessor 14 returns from the standby state and enters the activated state (F2). Next, the microprocessor 14 starts the sensing of the signal from the acceleration sensor 13 (F3) to put data of every walking cycle together to determine a walking mode (F4). One cycle of the walking can be decided by monitoring the signal of the pressure-sensitive sensor 12. The walking mode includes, for example, a normal walking mode and a step ascent mode. In the case of the step ascent mode, since the trajectory of the shoe is different from the trajectory during the normal walking, as shown in FIG. 4, the mode can be easily determined by obtaining the trajectory of the shoe based on the signal from the acceleration sensor 13.

When determined that it is the normal walking mode, stumbling determination is then carried out (F5). This stumbling determination is to determine if there is a possibility that a bottom of the shoe going forward scrapes the ground, although there is only little step ahead, and the user falls forward. This determination is enabled, for example, by calculating the lifting velocity and/or the lifting amount of the shoe from the signal of the acceleration sensor 13, and by comparing the value with a reference value. The lifting amount can be obtained by integrating the lifting velocity. The reference value may be a fixed value set in advance, but for example, data of the lifting velocity or the lifting amount of the foot may be accumulated after the shoe 1 is started to be used, and the reference value may be decided from an average value or a statistical value of the accumulated data. If the lifting velocity and/or the lifting amount is lower than the reference value, the microprocessor 14 determines that there is a possibility that the user stumbles, and activates the stimulator 11 (F6). Since the walker reflexively lifts the foot by the stimulation given to the bottom of the foot, the stumbling is avoided. If it is determined in the stumbling determination (F5) that there is no possibility of stumbling, the processing returns to the sensing of the signal of the acceleration sensor 13 (F3) without actuating the stimulator 11. In the normal walking mode, the ranging sensor 10 need not be actuated, and the processing can be simplified.

Figure 6:
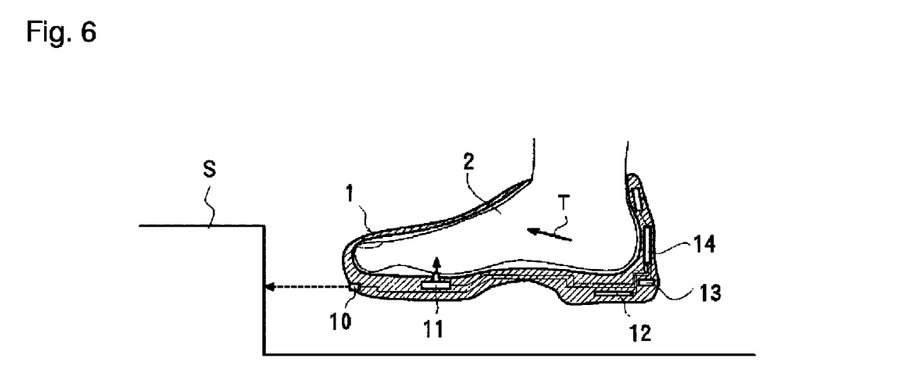
FIG. 6 is a diagram showing movement of the shoe when a person ascends the step.

On the other hand, if the step ascent mode is determined in the walking mode determination, the signal of the ranging sensor 10 is acquired as shown in FIG. 6 (F7) to measure the distance between the shoe 1 and the step (or the obstacle) S. Subsequently, collision determination is performed (F8). In the collision determination, the trajectory T of the shoe is calculated based on the detection signal of the acceleration sensor 13, and the collision time with the step S is instantly calculated from the calculated trajectory T and the measured distance. Based on these calculation results, for example, if the distance between the step S and the shoe is reduced after the predetermined time has passed, it is determined that there is a possibility that the shoe collides, and the stimulator 11 is immediately actuated (F6). When determined that the shoe will not collide, the processing returns to the sensing of the signal of the acceleration sensor 13 without actuating the stimulator 11 (F3), and loop processing is repeated until it is determined that the signal of the acceleration sensor 13 is not present for a predetermined period. When determined that the signal of the acceleration sensor 13 is not present for the predetermined time, the microprocessor 14 enters the standby state (F9). In FIG. 5, although the standby determination is performed in the walking mode determination as well, whether or not the microprocessor 14 should shift to the standby state may be determined in a step different from the walking mode.

In the processing algorithm in FIG. 5, the example has been described in which the walking mode is determined based on the signal from the acceleration sensor 13, and when determined as the normal walking mode, the signal from the ranging sensor 10 is not utilized. However, the signal from the ranging sensor 10 may be detected in the normal walking mode. For example, although there is some obstacle in front of the shoe, the walker may not notice the obstacle, and thus, when determined that the shoe will obviously collide with the obstacle, the microprocessor 14 may actuate the stimulator 11.

Figure 7:
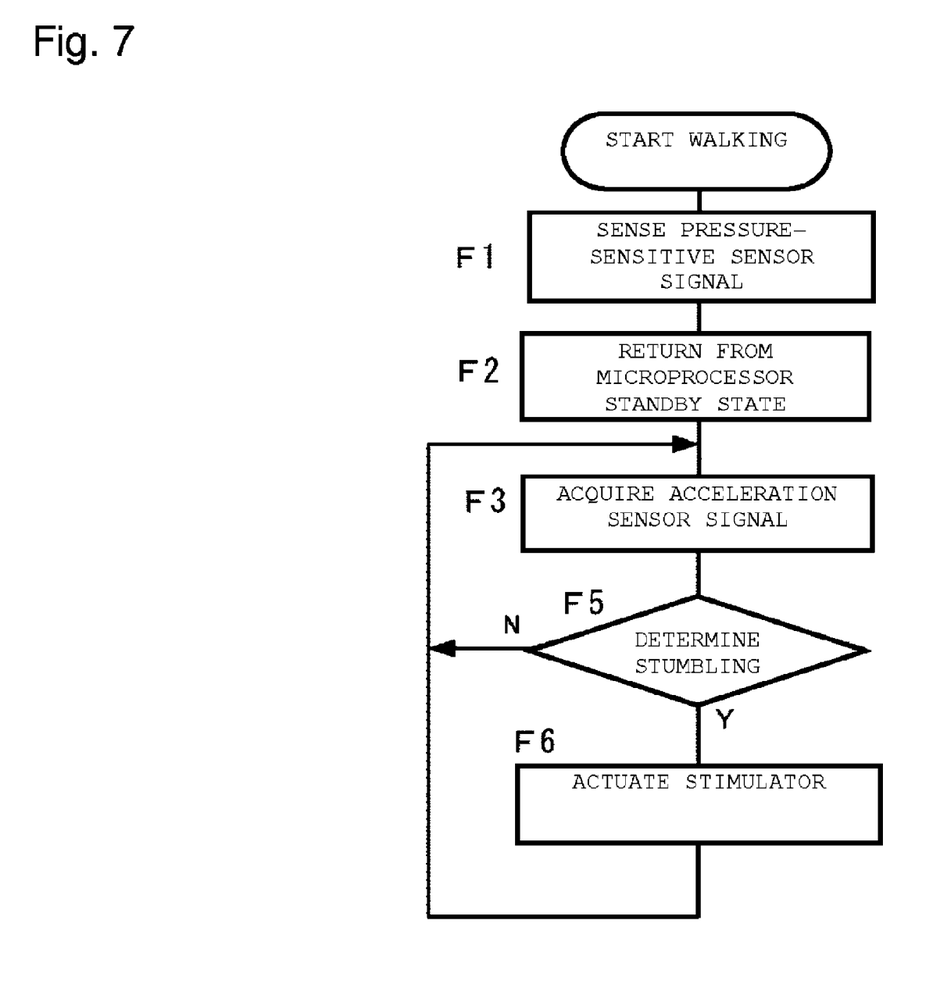
FIG. 7 is a flowchart showing another example of the processing algorithm of the microprocessor.

FIG. 7 shows an example of another processing algorithm of the present invention. While steps F1 to F3 are the same as those in FIG. 5, after the signal of the acceleration sensor 13 is acquired, only the stumbling determination is performed without determining the walking mode (F5). As a method of the stumbling determination, the lifting velocity and/or the lifting amount of the shoe may be calculated based on the signal from the acceleration sensor 13 to be compared with reference value, as in the foregoing. Further, the forward velocity of the shoe and the inclination angle of the shoe may be detected to be compared with reference values. In this case, since the ranging sensor 10 is not required, the circuit and the processing can be simplified.

Normally, the stumbling on a flat road, a step, stairs occurs because of slight insufficiency of the lifting amount of the shoe. Generally, the insufficiency is about 2 cm. Precise measurement is not required as to how much the shoe needs to be lifted to avoid the foregoing. Receiving the slight stimulation to the bottom of the foot causes the foot to be reflexively lifted by several centimeters, which allows the stumbling to be easily avoided.

In the above-described embodiment, only one of the shoes has been described, but the microprocessors each having a communication function may be included in both right and left shoes, and difference between the signals of the right and left shoes may be obtained to perform step determination. Synchronizing both the shoes also enables the walking abnormality to be detected. Furthermore, walking history data may be accumulated in the memory, and this data can be fetched so that walking history can be managed by a personal computer or the like. In the above-described embodiment, the pressure-sensitive sensor has been used as a trigger to activate the microprocessor, but for example, an ON/OFF switch may be provided in the shoe, and the microprocessor may be activated by operating this switch. Moreover, by one signal sensing of the pressure-sensitive sensor, the past processing may be reset to restart the processing.

DESCRIPTION OF REFERENCE SYMBOLS 1 shoe body
2 foot
10 ranging sensor
11 stimulator
12 pressure-sensitive sensor
13 acceleration sensor
14 microprocessor
15 battery
16 wiring

The invention claimed is:

1. A walking shoe comprising:
a shoe body configured to receive a foot;
a stimulator mounted on the shoe body in a position to stimulate a bottom of the foot;
an acceleration sensor mounted on the shoe body and configured to detect a first acceleration in a direction parallel to ground and a second acceleration in a direction perpendicular to the ground and generate an acceleration detection signal as a function thereof;
a range sensor mounted on the shoe body and configured to detect a distance between the shoe body and an obstacle and generate a range detection signal as a function thereof; and
a microprocessor mounted on the shoe body and configured to:
predict the trajectory of the user's foot as a function of the acceleration detection signal;
turn on the range sensor when the microprocessor determines that a trajectory of the user's foot indicates that the user is trying to lift his or her foot over an obstacle by comparing the trajectory to stored information indicative of a typical trajectory of the user's foot when he or she is walking; and
actuate the stimulator when the microprocessor determines that the user's foot is likely to hit the obstacle as a function of both the acceleration detection signal and the range detection signal, the microprocessor determining that the user's foot is likely to hit the obstacle when, a distance that the trajectory predicted that foot would be from the obstacle is less than an actual distance the foot is from the obstacle as indicated by the range detection signal.

2. The walking shoe according to claim 1, further comprising a pressure sensor mounted on the shoe body and configured to sense a pressure applied to the bottom portion of the shoe body and to generate a pressure signal as a function thereof, the microprocessor determining that the user is walking as a function of the pressure signal.

3. The walking shoe according to claim 2, wherein when the acceleration detection signal is not generated for a predetermined time after the microprocessor enters a standby state, and when the pressure sensor determines that the user has begun walking as a function of the pressure signal, the microprocessor returns to an activated state.

4. The walking shoe according to claim 1, wherein the microprocessor causes information about the trajectory of the user's foot when the user is walking to be stored in memory by periodically sampling the acceleration detection signal.

5. The walking shoe of claim 4, wherein the microprocessor causes the information about the trajectory of the user's foot when the user is walking to be stored in the memory as a function of the trajectory occurring most frequently when the user is walking.

* * * * *